United States Patent [19]

Pässler et al.

[11] Patent Number: 5,789,644
[45] Date of Patent: Aug. 4, 1998

[54] PREPARATION OF ACETYLENE AND SYNTHESIS GAS

[75] Inventors: Peter Pässler, Ludwigshafen; Rainer Feser, Grünstadt; Hans-Günter Thelen, Dossenheim, all of Germany

[73] Assignee: BASF Aktiengesellschaft, Ludwigshafen, Germany

[21] Appl. No.: 468,068

[22] Filed: Jun. 6, 1995

[30] Foreign Application Priority Data

Jun. 29, 1994 [DE] Germany .................. 44 22 815.5

[51] Int. Cl.[6] .................. C07C 2/02; C07C 1/02; C10G 9/04
[52] U.S. Cl. .................. 585/534; 585/534; 585/539; 585/540; 585/538; 48/216; 48/127.9; 48/198; 252/373
[58] Field of Search .................. 585/540, 539, 585/534, 538; 48/127.9, 216, 198; 252/373

[56] References Cited

U.S. PATENT DOCUMENTS 3,242,224  3/1966  Howard .................. 260/679
3,825,400  7/1974  Popov .................. 431/160
5,087,270  2/1992  Gateau .................. 48/127.9

FOREIGN PATENT DOCUMENTS 2226891    11/1974  France .
12 59 875   7/1960  Germany .
1126858    10/1960  Germany .
29 47 005   6/1981  Germany .

Primary Examiner—Glenn Caldarola
Assistant Examiner—Tanaga Ann Boozer
Attorney, Agent, or Firm—Keil & Weinkauf

[57] ABSTRACT

In the preparation of acetylene and synthesis gas by partial oxidation of hydrocarbons with oxygen, the feedstock gases are first separately preheated, then intensively mixed in a mixing zone, reacted after flowing through a burner block and then rapidly cooled.

The burner block has a number of continuous ducts. According to the invention the ducts of the burner block are covered on the inlet side by plates furnished with perforations.

4 Claims, 2 Drawing Sheets

PREPARATION OF ACETYLENE AND SYNTHESIS GAS

The invention relates to a process for preparing acetylene and synthesis gas by partial oxidation of hydrocarbons with oxygen, the feedstock gases being first preheated separately, intensively mixed in a mixing zone, reacted after flowing through a burner block and then rapidly cooled, the burner block having a number of continuous ducts.

The preparation of acetylene and synthesis gas by partial oxidation of hydrocarbons has been described many times in the past (see inter alia DE 12 59 875, DE 29 47 005, U.S. Pat. No. 3,242,224). The partial oxidation of methane (natural gas) to acetylene and synthesis gas has thus in particular achieved industrial importance internationally. Whereas preparation of synthesis gas alone from natural gas by partial oxidation is an industrially simple process, the synthesis gas process coupled to acetylene preparation is associated with precise spatial, time and volumetric conditions. Thus the starting materials natural gas and oxygen are normally preheated separately substantially to 700 degrees Celsius, intensively mixed in a mixing zone and are reacted after flowing through a burner block. The volume ratio of oxygen to natural gas used is about 0.6.

The burner block comprises a defined number of ducts in which the velocity of the reactive oxygen/natural gas mixture is higher than the flame velocity in order to prevent flame blow back into the mixing compartment. The reaction compartment following the burner block is of such a size that at a defined starting material flow rate, the residence time of the acetylene-containing reaction gas, the cracked gas, is only a few milliseconds. After this time, during which the equilibria corresponding to the temperature level of 1500 to 2000 degrees Celsius cannot be established, the reaction products are quenched substantially instantaneously to below 300 degrees Celsius with water or preferably residue oil, so that the acetylene formed does not decompose into soot and hydrogen. Usually, these processes operate at atmospheric pressure or slightly elevated pressure. In addition to natural gas, all gaseous or readily volatile hydrocarbons can be used under somewhat altered process conditions. However, all process variants have the disadvantage that a reactor size once calculated or empirically determined establishes the capacity for acetylene and crude synthesis gas in defined limits, the ratio of acetylene to synthesis gas remaining almost constant. This leads to the fact that when the acetylene requirement decreases, the production of the coupled product synthesis gas also decreases and thus the production of interconnected plants, such as methanol production, also decreases.

It is the object of the present invention to improve the known processes for preparing acetylene and synthesis gas by partial oxidation of hydrocarbons in such a manner that in the coupled production of acetylene and synthesis gas the ratio between the acetylene produced and the synthesis gas can be varied within broad ranges.

We have found that this object is achieved by the ducts of the burner block being covered on the inlet side by a plate furnished with perforations.

The process according to the invention makes it possible to vary the oxygen to hydrocarbon ratio within broad ranges without preignition occurring. Whereas in known processes this ratio can only be varied within narrow ranges, the process according to the invention surprisingly enables the ratio to be increased to such an extent that the content of acetylene in the cracked gas is greatly decreased. It is obvious that the process according to the invention which can be carried out by modifying an existing known burner block can be changed over from high to low acetylene production without any complication. That is it can be changed over from a low to a high starting material ratio which gives the burner an extraordinary adaptability. This is of very great importance in practice.

With gas velocities of from 50 to 150 m/s, preferably 100 m/s in the tubular ducts of the burner block (block tubes) and from 100 to 300, preferably 200, m/s in the perforated plate, corresponding to an area ratio of 2 to 1, a burner block furnished with a defined number of ducts and thus the burner (reactor) has a high capacity range and thus adaptability to product requirements.

The diameter and the number of ducts determine the nominal capacity of a burner block or burner. According to the invention, duct is diameters of from 15 to 45 mm are technically interesting, preferably of from 20 to 35 mm. Their number is from 50 to 150, preferably 127. The boreholes of the perforated cover plate have a diameter of from 2.5 to 7 mm, preferably of from 3 to 6 mm.

Further details and advantages of the invention can be taken from the illustrative example described with reference to the drawing. In the figures.

Figure 1:
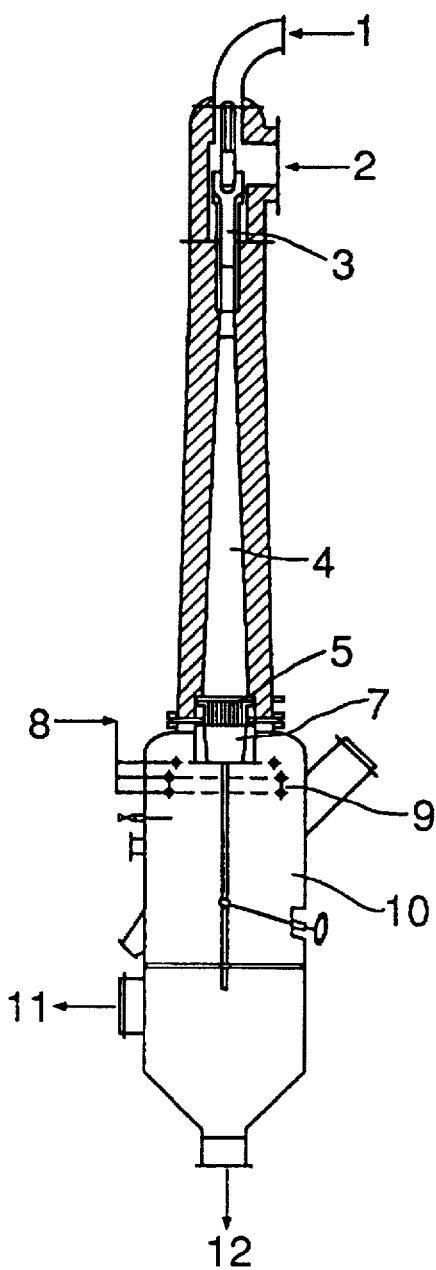
FIG. 1 shows a diagram of known equipment for carrying out partial oxidation.
Figure 2:
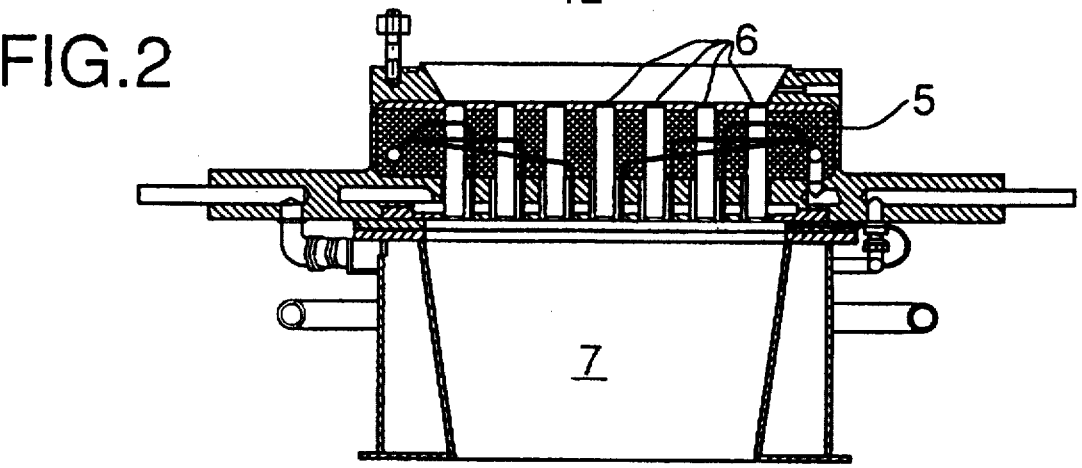
FIG. 2 shows an enlargement of a section through the burner block of FIG. 1.

The known equipment shown in FIGS. 1 and 2 is taken from "Ullmann's Encyclopedia of Industrial Chemistry, Vol. A1, 1985", page 107. Oxygen is fed to this equipment through line 1 and hydrocarbon through line 2 in a preheated state. The components are mixed in zone 3 so rapidly that no areas result having an oxygen concentration high enough that preignition could occur. The mixture is then conducted through a diffuser 4 to the burner block 5 and through its ducts 6 to the reaction zone 7. The mixture is there instantaneously and uniformly ignited using a multiplicity of auxiliary flames which exit from the lower side of the burner block, i.e. at the beginning of the reaction compartment.

A coolant is fed through line 8 via the quench tube 9 to the interior of the quench vessel 10. The cracked gas leaves the equipment through line 11. 12 is the outlet for the coolant used for quenching.

No details of the burner block 5 shown in FIG. 2 will be given; the only point which appears essential here with respect to the invention is that parallel ducts 6 comprising boreholes are provided which connect the diffuser 4 to the reaction compartment 7.

Figure 3:
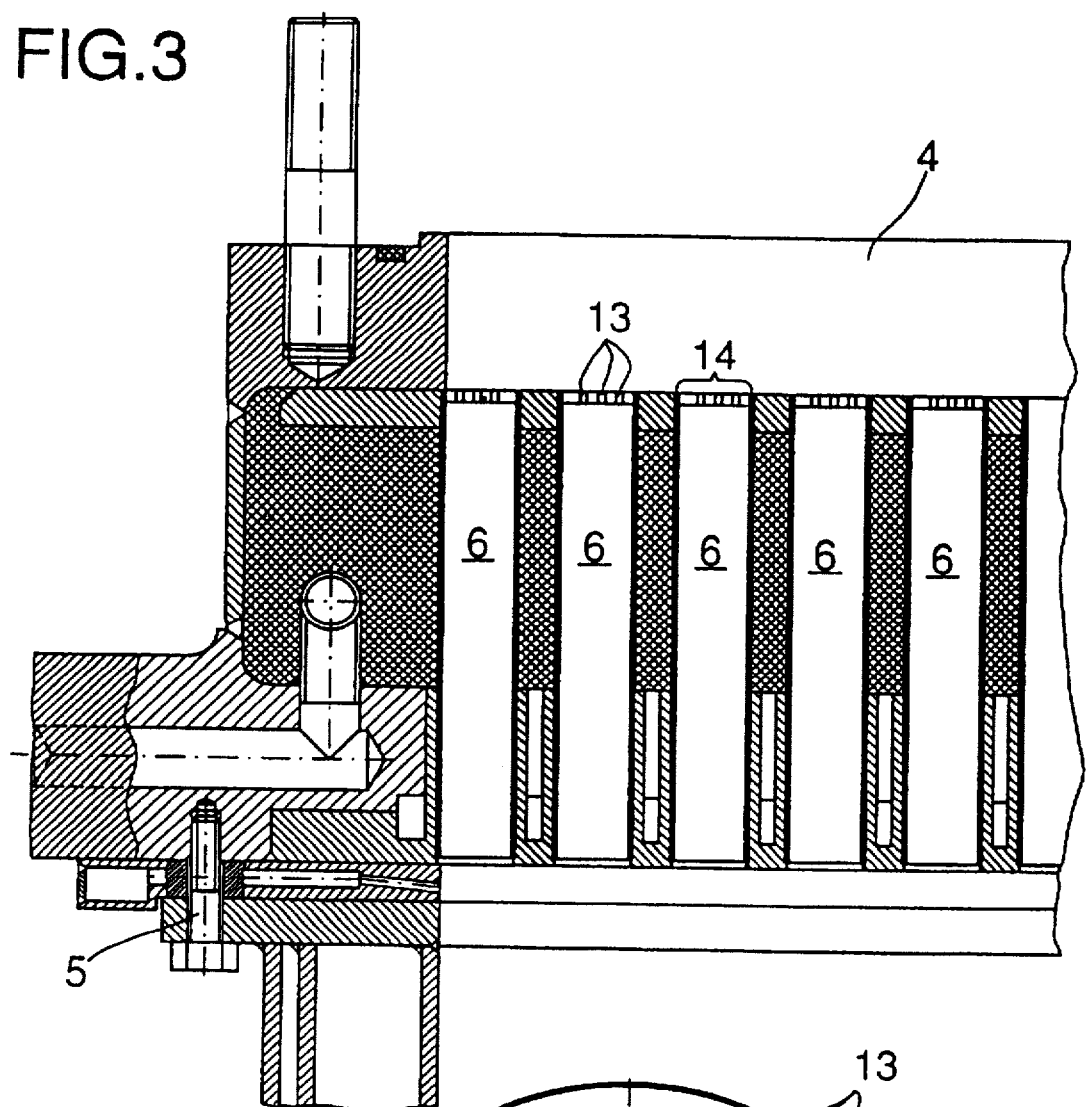
FIG. 3 shows a greatly enlarged detail of a burner block for carrying out the process according to the invention.
Figure 4:
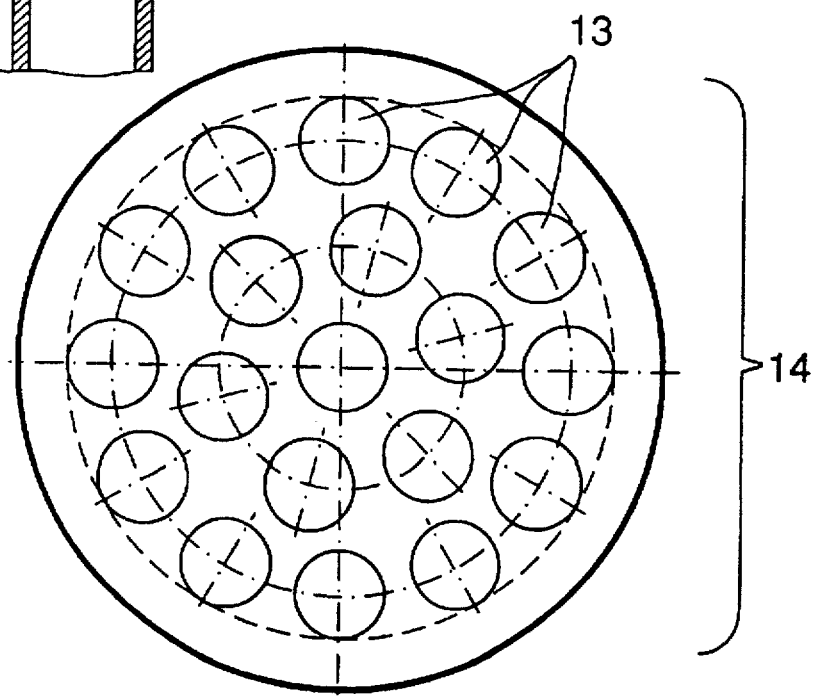
FIG. 4 shows a plan view of a cover plate according to the invention.

FIG. 3 shows an enlarged and simplified section through a burner block 5 corresponding to FIG. 2. The difference essential to the invention to the known burner block is that the ducts 6 are covered by a plate 14 at the top end opposite to the reaction compartment 7 and the plate is furnished with boreholes 13 regularly distributed over its cross section. The diameters of the ducts 6 are generally from 15 mm to 45 mm, the diameter of the perforations is from 2.5 mm to 7 mm, preferably about 4 mm. The thickness of the plate 14 can be from 2 mm to 8 mm, preferably about 3 mm.

The plate material must be heat-resistant.

Instead of covering the burner block ducts individually with perforated plates, in existing equipment a plate covering the entire burner block can alternatively be provided which is only furnished with corresponding boreholes at points where the burner block ducts open out. In a particularly simple manner, the entire plate can also be furnished with boreholes in such a manner that the number of boreholes which is required according to the invention over each end of the ducts is present.

In the examples below, a steel burner block was used the ducts of which, having a diameter of 27 mm, were each covered by a perforated plate in such a manner that 19 boreholes each of diameter 4.2 mm were allotted to each block tube.

The plate thickness was 3 mm and the material was Incoloy 800.

EXAMPLES 1 TO 8

In all of the examples listed in the table below, the starting materials natural gas and oxygen were heated separately to 600 degrees Celsius, mixed intimately in a mixer 3 and were reacted after passing through a diffuser 4 and the burner block 5. After a reaction time of a few milliseconds, the acetylene-containing cracked gases were quenched to about 250 degrees Celsius by a heavy aromatic oil and then fractionated into the products acetylene and crude synthesis gas in a known manner by fractional absorption and subsequent desorption using a suitable solvent.

| Trial | 1 | 2 | 3 | 4 | 5 | 6 | 7 | 8 |
|---|---|---|---|---|---|---|---|---|
| $m^3$ (S.T.P)/h of oxygen | 4267 | 4255 | 4268 | 4264 | 3669 | 3674 | 3662 | 3668 |
| $m^3$ (S.T.P.)/h of natural gas | 6699 | 6207 | 5709 | 5216 | 5714 | 5294 | 4970 | 4544 |
| ratio of oxygen to natural gas | 0.637 | 0.686 | 0.748 | 0.817 | 0.642 | 0.694 | 0.737 | 0.807 |
| % by volume of acetylene in the cracked gas | 7.45 | 4.56 | 1.54 | 1.45 | 6.91 | 4.15 | 1.81 | 1.43 |
| Kg/h of acetylene | 1134 | 701 | 239 | 233 | 903 | 557 | 236 | 181 |
| $m^3$ (S.T.P.)/h of synthesis gas | 11990 | 12500 | 13011 | 13468 | 10359 | 10965 | 10917 | 10629 |
| $m^3$ (S.T.P.) of synthesis gas per ton of acetylene | 10573 | 17832 | 54439 | 57802 | 11472 | 19686 | 46258 | 58724 | burner block having a number of continuous ducts, and then rapidly cooled, wherein the improvement comprises the step of:

covering the ducts of the burner block on the inlet side with selected plates having perforations, whereby the ratio between the acetylene produced and synthesis gas can be varied within a broad range based on selected perforation size.

2. A process as claimed in claim 1, wherein with a duct diameter (6) of from 15 mm to 45 mm, preferably of from 20 to 35 mm, the diameters of the perforations (13) are from 2.5 mm to 7 mm, preferably from about 3 to 6 mm.

3. A process as claimed in claim 2, wherein each individual duct (6) has on the inlet side a separate plate (14) having perforations (13).

We claim:

1. An improved process for preparing acetylene and synthesis gas by partial oxidation of hydrocarbons with oxygen, in which the feedstock gases are first preheated separately, intensively mixed in a mixing zone, reacted in a 4. A process as claimed in claim 1, wherein each individual duct (6) has on the inlet side a separate plate (14) having perforations (13).

* * * * *